United States Patent [19]

Marfat

[11] Patent Number: 5,116,854

[45] Date of Patent: May 26, 1992

[54] ANTI-INFLAMMATORY 1-HETEROARYL-3-ACYL-2-OXINDOLES

[75] Inventor: Anthony Marfat, Mystic, Conn.

[73] Assignee: Pfizer Inc., New York, N.Y.

[21] Appl. No.: 688,600

[22] Filed: Jun. 28, 1991

[51] Int. Cl.$^5$ ............... C07D 407/04; C07D 409/04; C07D 417/04; A61K 31/40
[52] U.S. Cl. .................... 514/365; 514/414; 548/181; 548/465; 548/468
[58] Field of Search ............ 548/181, 465, 468; 514/414, 365

[56] References Cited

U.S. PATENT DOCUMENTS 4,053,613 10/1977 Rovnyak .................. 514/414
4,752,609 6/1988 Kadin ...................... 514/339

Primary Examiner—Robert Gerstl
Attorney, Agent, or Firm—Peter C. Richardson; Paul H. Ginsburg; Grover F. Fuller, Jr.

[57] ABSTRACT

Certain 1-heteroaryl-3-acyl-2-oxindoles wherein the acyl-substituent is thenoyl, furoyl, benzoyl or substituted benzoyl, are inhibitors of cycloxygenase and lipoxygenase enzymes and are useful as anti-inflammatory agents in mammals.

16 Claims, No Drawings

ANTI-INFLAMMATORY 1-HETEROARYL-3-ACYL-2-OXINDOLES

BACKGROUND OF THE INVENTION

1. Field of the Invention

This invention relates to new and useful nonsteroidal anti-inflammatory agents. More particularly, it relates to certain 1-heteroaryl-3-acyl-2-oxindoles which are potent inhibitors of cyclooxygenase (CO) and lipoxygenase (LO) and which are of value as anti-inflammatory agents in mammals.

1. Description of Related Art

U.S. Pat. No. 4,556,672, issued Dec. 3, 1985, describes a series of 3-acyl-2-oxindole-1-carboxamides in which the acyl group, —C(=O)R, is derived from a wide variety of organic carboxylic acids, including those wherein R is phenyl, substituted phenyl, thienyl, furyl or other heterocyclyl groups. The compounds are useful as analgesics and anti-inflammatory agents. Related compounds in which the 1-carboxamide group is substituted by alkyl, phenyl, substituted phenyl, furyl or thienyl are described in U.S. Pat. No. 4,569,942, issued Feb. 11, 1986, as having the same utility. Also disclosed in each of said patents are 3-acyl-2-oxindoles wherein the acyl group is as defined above.

Analgesic and anti-inflammatory 1,3-diacyl-2oxindoles wherein the 1-acyl group is an alkanoyl group and the 3-acyl group is as disclosed in the above-mentioned patents are described in U.S. Pat. No. 4,690,943, issued Sep. 1, 1987.

SUMMARY OF THE INVENTION

It has been found that certain 1-heteroaryl-3-acyl-2-oxindoles of formula (I)

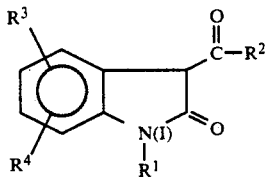

or a pharmaceutically acceptable base salt thereof wherein
$R^1$ is thienyl, furyl or 2-thiazolyl;
$R^2$ is thienyl, furyl or

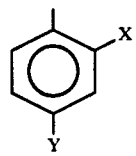

wherein X is hydrogen, fluoro, chloro, alkyl having 1 to 4 carbon atoms, alkoxy having 1 to 4 carbon atoms, alkylthio having 1 to 4 carbon atoms, nitro or trifluoromethyl;
Y is hydrogen, fluoro or chloro;
and each of $R^3$ and $R^4$, which may be alike or different, is hydrogen, fluoro, chloro, bromo, alkyl having 1 to 4 carbon atoms, alkoxy having 1 to 4 carbon atoms, alkylthio having 1 to 4 carbon atoms, nitro or trifluoromethyl are potent inhibitors of CO and LO enzymes, and are of value as anti-inflammatory agents for treating an inflammatory disease in a mammal. They are especially useful for treatment of rheumatoid arthritis in mammals.

A favored group of compounds are those wherein $R^2$ is phenyl or substituted phenyl. Within this group of compounds those wherein one or both of X and Y are hydrogen, fluoro, chloro or trifluoromethyl are preferred compounds. Especially preferred in this group are those compounds wherein each of X and Y is hydrogen, or X is 5-chloro and Y is 6-chloro, and $R^1$ is a 3-heteroaryl group.

Another favored group of compounds embraces those wherein $R^2$ is thienyl or furyl. Preferred within this group are those wherein $R^2$ is 2-thienyl or 2-furyl and $R^1$ is a 3-heteroaryl group.

Included within this invention are pharmaceutical compositions, useful as anti-inflammatory agents in a mammal, comprising a pharmaceutically acceptable carrier and an anti-inflammatory disease treating amount of a compound of formula (I).

Additionally, the present invention includes a method of treating an anti-inflammatory disease in a mammal which comprises administering to said mammal an anti-inflammatory disease treating amount of a compound of formula (I).

DETAILED DESCRIPTION OF THE INVENTION

The compounds of this invention are readily prepared from appropriate reactants by the following process:

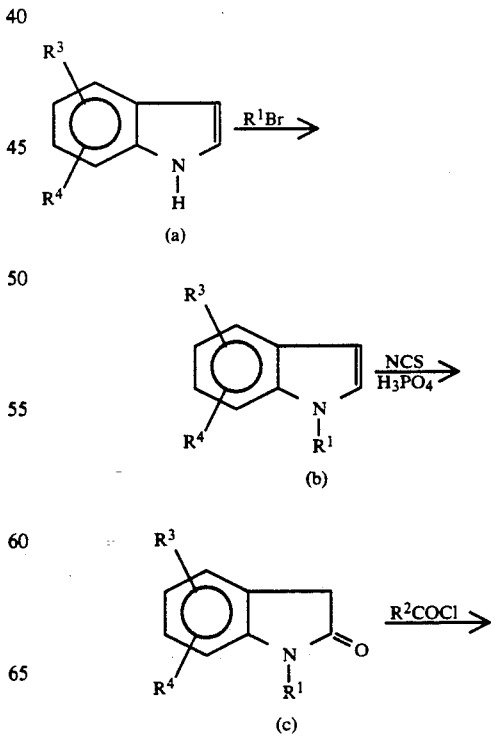

-continued

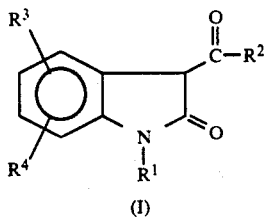
(I)

The first step of the overall process is carried out by reacting indole (or an appropriately substituted indole) with the desired $R^1Br$ in a suitable solvent in the presence of a base and a catalytic amount of cuprous bromide. As solvent, N-methyl-2-pyrrolidinone serves especially well. Other aprotic solvents such as dimethylsulfoxide, dimethylformamide or diethylformamide can be used. The reaction is conducted at an elevated temperature, e.g. from about 50° C. to 200° C., desirably under a nitrogen atmosphere. The choice of base is not critical, but can be any of a variety of inorganic and organic bases. Representative of such bases are alkali metal hydrides, carbonates or hydroxides; triethylamine, pyridine, N-methylmorpholine, 4-(N,N-dimethylamino)-pyridine and N-methylpiperidine.

The above-named ingredients are all generally placed in a reaction vessel, stirred and heated to the desired temperature until reaction is complete. Although the indole, $R^1Br$, and base reactants can be used in stoichiometric proportions, it is preferred to use about 5–10% excess of each of $R^1Br$ and base in order to expedite the reaction. A greater excess of $R^1Br$, e.g., up to 100%, can be used but is generally avoided for economic reasons. The cuprous bromide is employed at a level of from about 0.01 to 0.03 moles per mole of $R^1Br$ reactant. The product is recovered by known methods. The required indole reactants are known compounds or are conveniently prepared according to known procedures.

The second step, conversion of the 1-substituted indole (b) to the corresponding oxindole (c) is accomplished by reacting indole (b) with N-chlorosuccinimide (NCS) in a reaction-inert solvent at ambient temperature. A 5–10% excess of NCS is generally used. Reaction periods of from 1 to 5 hours, depending upon the indole (a) reactant normally lead to complete reaction. The reaction-inert solvent (i.e., one which does not react with reactants or products) can be any of a variety of solvents, such as diethyl ether, dioxane, tetrahydrofuran, aromatic hydrocarbons, (benzene, toluene, xylene), chloroform, acetonitrile and mixtures thereof.

Upon completion of the NCS reaction, the reaction is concentrated under reduced pressure and the 3-chloro indole derivative taken up in glacial acetic acid and heated to from about 50°–80° C. Phosphoric acid (85%) is then added to the reaction which is refluxed for 1–24 hours, cooled and poured into ice-water. The aqueous mixture is adjusted to pH 11–12 and then extracted with ethyl acetate to recover the oxindole. Work-up of the extract and purification of the oxindole product is by standard methods.

Introduction of the acyl moiety at the 3-position of oxindole (c) is conveniently accomplished by reacting (c) with an activated derivative of the appropriate carboxylic acid of formula $R^2$—COOH in a lower alkanol solvent (e.g. ethanol) in the presence of an alkali metal salt of the lower alkanol solvent (e.g. sodium ethoxide) according to standard procedures. Typical derivatives of the acids include acid halides, e.g., acid chlorides; symmetrical acid anhydrides, $R^2$—C(=O)—O—C(=O)—$R^2$; mixed acid anhydrides with a hindered low-molecular weight carboxylic acid, $R^2$—C(=O)—O—C(=O)—$R^5$, where $R^5$ is a bulky lower-alkyl group such as t-butyl; and mixed carboxylic-carbonic anhydrides, $R^2$—C(=O)—O—C(=O)—$OR^6$, wherein $R^6$ is a lower-alkyl group. Usually, a small excess of the derivative of the acid of formula $R^2$—C(=O)—OH is used, and the alkoxide salt is usually present in an amount from one to two molar equivalents, based on said derivative of the acid of formula $R^2$—C(=O)—OH. The reaction between the derivative of the acid of the formula $R^2$—C(=O)—OH and the compound of formula (c) is usually started at 0° to 25° C., but it is then usual to heat the reaction mixture at a temperature in the range from 50° to 130° C., and preferably at about 80° C., to complete the reaction. Under these circumstances, reaction times of a few hours, e.g., two hours, up to a few days, e.g., two days, are commonly used. The reaction mixture is then cooled, diluted with an excess of water and acidified. The product of formula (I) can then be recovered by filtration or by the standard procedure of solvent extraction.

A common characteristic of the oxindole carboxamides of this invention is their acidic nature. Therefore, included in this invention are the pharmaceutically acceptable salts of the compounds of formula (I). The preferred cations of said salts include the ammonium, sodium and potassium ions. The pharmaceutically acceptable salts of the compounds described herein are prepared by conventional procedures, as for example, by adding the acid to an aqueous solution containing an equivalent amount of the pharmaceutically acceptable base, i.e., a base containing one of the above preferred cations, followed by concentration of the resultant mixture to obtain the desired product. The bases can be selected from hydroxides, oxides or carbonates.

Also considered part of the present invention are prodrugs of the herein described compounds of formula (I). These prodrugs, which have fewer gastrointestinal side effects, break down in situ to the parent compound. Representative prodrugs of formula (I) compounds are enol esters and ethers thereof of formula (II)

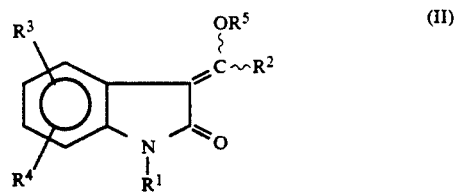
(II)

wherein each of $R^1$, $R^2$, $R^3$ and $R^4$ is as defined above; and $R^5$ is alkanoyl, cycloalkylcarbonyl, phenylalkanoyl, chlorobenzoyl, methoxybenzyl, phenyl, thenoyl, omegaalkoxycarbonylalkanoyl, alkoxycarbonyl, phenoxycarbonyl, 1-alkoxyalkyl, 1-alkoxycarbonyloxyalkyl, alkyl, alkylsulfonyl, methylphenylsulfonyl or dialkylphosphonate.

In formula (II), the wavy lines on the carbon atom of the exocyclic double bond at the 3-position are intended to represent the syn-, the anti- and mixtures of the syn- and anti- forms of formula (II) compounds.

Formula (II) compounds are prepared by treating the appropriate 3-acyl 2-oxindole of formula (I) and an equimolar amount of triethylamine in a reaction-inert solvent (e.g., chloroform) with a slight excess of the requisite acid chloride, chloroformate, oxonium salt or alkylating agent at 0° C. The reaction is allowed to warm to room temperature and, after 2-3 hours, the product is recovered by known procedures.

A second procedure for preparation of formula (II) compounds consists of contacting, in an anhydrous reaction-inert solvent such as acetone, the appropriate 3-acyl-2-oxindole of formula (I), a three-fold molar excess of the requisite alpha-chloroalkylcarbonate, a five-fold molar excess of sodium iodide and a two-fold molar excess of anhydrous potassium carbonate and heating said reaction mixture at reflux for 16 hours.

The reaction mixture is diluted with water and the product extracted with a water-immiscible solvent, such as diethyl ether or chloroform. Concentration of the solvent containing the product provides the crude material, which can be purified by recrystallization and/or chromatography.

As previously indicated, the oxindole carboxamides of the present invention and their pharmaceutically acceptable salts are useful anti-inflammatory agents in mammals. These compounds are of value in alleviating swelling and inflammation which are symptomatic of rheumatoid arthritis and related disorders which are responsive to treatment with anti-inflammatory agents. Either as individual therapeutic agents or as mixtures of therapeutic agents, they may be administered alone, but are generally administered with a pharmaceutical carrier selected on the basis of the chosen route of administration and standard pharmaceutical practice. For example, they may be administered orally in the form of tablets or capsules containing such excipients as starch, milk sugar or certain types of clay, etc. They may be administered orally in the form of elixirs or oral suspensions with the active ingredients combined with emulsifying and/or suspending agents. They may be injected parenterally, and for this use they, or appropriate derivatives, may be prepared in the form of sterile aqueous solutions. Such aqueous solutions should be suitably buffered, if necessary, and should contain other solutes such as saline or glucose to render them isotonic. The weight-ratio of the pharmaceutically-acceptable carrier to compound can be from 1:4 to 20:1.

The dosage required to reduce inflammation or swelling in arthritic subjects would be determined by the nature and extent of the symptoms. Generally, small doses will be required initially, with a gradual increase in the dose until the optimum level is determined. It will generally be found that when the composition is administered orally, larger amounts of the active ingredient will be required to produce the same level as produced by a smaller quantity administered parenterally. In general, from about 10 to about 300 mg of active ingredient per kilogram of body weight, administered orally in single or multiple dose units, will effectively reduce inflammation and swelling. Parenteral administration requires doses of from about 5 to about 200 mg of active ingredient to achieve the same end point.

A standard procedure for detecting and comparing anti-inflammatory activity of compounds is the carrageenin rat foot edema test, which is described by C. A. Winter et al., Proc. Soc. Exp. Biol. vol III, page 544 (1962).

In addition to being useful as anti-inflammatory agents, the compounds of the present invention can be used in the treatment of asthma, bronchitis and psoriasis; they can also be used as analgesic agents.

The following examples are provided solely for the purpose of further illustration. Nuclear magnetic resonance spectra (NMR) were measured at 60 MHz for solutions in deuterochloroform ($CDCl_3$) and peak positions are expressed in parts per million (ppm) downfield from tetramethylsilane or sodium 2,2-dimethyl-2-silapentane-5-sulfonate. The following abbreviations for peak shapes are used: s, singlet; d, doublet; t, triplet; q, quartet; m, multiplet; b, broad.

EXAMPLE 1

1-(2-Thiazolyl)-3-(2-furoyl)-2-oxindole

To a solution of 1-(2-thiazolyl)-2-oxindole (0.6 g, 2.7 mM) in dimethylformamide (8 ml) at 0° C. was added 4-dimethylaminopyridine (0.847 g, 2.2 eq.) and the mixture stirred for 5 minutes. Then, a solution of 2-furoyl chloride (0.31 ml, 3.04 mM, 1.1 eq.) in dimethylformamide (2 ml) was added dropwise and the mixture stirred for 15 minutes at 0° C. and then at room temperature for 2 hours. The reaction was poured onto about 100 ml of ice/2N HCl, and the resulting yellow precipitate recovered by filtration, washed with water and air-dried. Recrystallization from toluene-hexane (1:1) afforded 0.585 g (64%) of title product as yellow needles; m.p. 156°-157° C.

In like manner the following compounds were prepared from appropriate reactants.

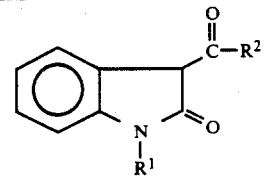

| $R^1$ | $R^2$ | (m.p. °C.) |
| --- | --- | --- |
| 2-thiazolyl | 2-thienyl | 168-9 |
| 3-thienyl | 2-furyl | 132-3 |
| 3-thienyl | 2-thienyl | 130-2 (dec.) |

EXAMPLE 2

Following the procedure of Example 1, the compounds listed below are prepared from appropriate reactants:

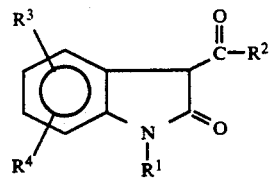

| $R^3$ | $R^4$ | $R^1$ | $R^2$ |
| --- | --- | --- | --- |
| H | H | 2-thiazolyl | $C_6H_5$ |
| H | H | 2-thiazolyl | $4-FC_6H_4$ |
| H | H | 2-thiazolyl | $4-ClC_6H_4$ |
| H | H | 2-thiazolyl | $2,4-F_2C_6H_3$ |
| H | H | 2-thiazolyl | 3-thienyl |
| H | H | 2-thiazolyl | $2-CF_3C_6H_4$ |
| H | H | 2-thiazolyl | $4-CH_3C_6H_4$ |
| H | H | 2-thiazolyl | $4-CH_3O-6-ClC_6H_3$ |
| H | H | 2-thiazolyl | $2,6-(CH_3)_2C_6H_3$ |
| H | H | 2-thiazolyl | $4-NO_2C_6H_4$ |
| H | H | 2-thiazolyl | $4-(CH_3S)C_6H_4$ |
| 5-Cl | H | 2-thiazolyl | 2-thienyl |
| 5-Cl | H | 2-thiazolyl | 3-furyl |

-continued

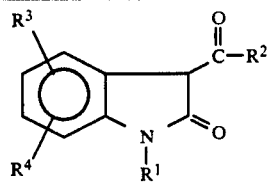

| R³ | R⁴ | R¹ | R² |
|---|---|---|---|
| 6-F | H | 2-thiazolyl | $C_6H_5$ |
| H | 7-F | 2-thiazolyl | $2,4\text{-}Cl_2C_6H_3$ |
| 5-F | 6-F | 2-thiazolyl | $4\text{-}FC_6H_4$ |
| H | 7-$C_2H_5$ | 2-thiazolyl | 3-thienyl |
| 4-$OCH_3$ | H | 2-thiazolyl | 2-furyl |
| H | 6-$CF_3$ | 2-thiazolyl | $4\text{-}ClC_6H_4$ |
| H | H | 3-thienyl | $C_6H_5$ |
| H | H | 3-thienyl | $4\text{-}ClC_6H_4$ |
| H | H | 3-thienyl | $4\text{-}FC_6H_4$ |
| H | H | 3-thienyl | $2,4\text{-}Cl_2C_6H_3$ |
| H | H | 3-thienyl | $2\text{-}CF_3C_6H_4$ |
| 5-Cl | H | 3-thienyl | $4\text{-}(C_2H_5O)C_6H_4$ |
| 5-F | H | 3-thienyl | 3-thienyl |
| 5-F | 6-F | 3-thienyl | 3-thienyl |
| 5-$NO_2$ | H | 3-thienyl | 2-furyl |
| 4-$OCH_3$ | 6-$OCH_3$ | 3-thienyl | $C_6H_5$ |
| 5-$OCH_3$ | 6-Cl | 3-thienyl | $4\text{-}FC_6H_4$ |
| 5-$CF_3$ | H | 3-thienyl | 2-furyl |
| 5-Br | H | 3-thienyl | $C_6H_5$ |
| 6-i-$C_3H_7$ | H | 3-thienyl | $4\text{-}ClC_6H_4$ |
| H | H | 3-thienyl | $4\text{-}(CH_3S)C_6H_4$ |
| H | H | 2-thienyl | 3-thienyl |
| 4-$SCH_3$ | H | 2-thienyl | 3-furyl |
| 5-Cl | 6-Cl | 2-thienyl | $C_6H_5$ |
| 6-F | H | 2-thienyl | $C_6H_5$ |
| 5-$OCH_3$ | 6-F | 2-thienyl | $C_6H_5$ |
| 4-$C_2H_5$ | H | 2-thienyl | 3-thienyl |
| 5-Cl | 6-Cl | 2-thienyl | 2-thienyl |
| 5-Br | H | 2-thienyl | $C_6H_5$ |
| 4-$OCH_3$ | 7-$OCH_3$ | 2-thienyl | $2,4\text{-}F_2C_6H_3$ |
| 5-$CF_3$ | H | 2-thienyl | 2-thienyl |
| 5-$CH_3$ | 7-Cl | 2-thienyl | $4\text{-}(CH_3O)C_6H_4$ |
| H | H | 3-furyl | 3-thienyl |
| H | H | 3-furyl | 3-furyl |
| H | H | 3-furyl | $C_6H_5$ |
| H | H | 3-furyl | $4\text{-}ClC_6H_4$ |
| H | H | 3-furyl | $2,4\text{-}C_6H_3$ |
| H | H | 3-furyl | $4\text{-}ClC_6H_4$ |
| 5-F | 6-F | 3-furyl | $C_6H_5$ |
| H | 6-F | 3-furyl | $C_6H_5$ |
| 5-Cl | H | 3-furyl | $C_6H_5$ |
| 5-$CH_3$ | H | 3-furyl | $4\text{-}FC_6H_4$ |
| 5-$OCH_3$ | 6-Cl | 3-furyl | $4\text{-}ClC_6H_4$ |
| 5-$CH_3$ | 6-$CH_3$ | 3-furyl | $4\text{-}FC_6H_4$ |
| 5-$CF_3$ | H | 3-furyl | $2,4\text{-}F_2C_6H_3$ |
| 5-$NO_2$ | H | 3-furyl | $2\text{-}ClC_6H_4$ |
| H | H | 2-furyl | 2-thienyl |
| H | H | 2-furyl | 3-furyl |
| H | H | 2-furyl | $C_6H_5$ |
| H | H | 2-furyl | $2\text{-}FC_6H_4$ |
| H | H | 2-furyl | $4\text{-}ClC_6H_4$ |
| 5-F | 6-F | 2-furyl | $C_6H_5$ |
| H | 6-Cl | 2-furyl | $4\text{-}ClC_6H_4$ |
| 5-$OCH_3$ | 6-F | 2-furyl | $4\text{-}FC_6H_4$ |
| H | 7-i-$C_4H_9$ | 2-furyl | $2,4\text{-}F_2C_6H_3$ |
| H | 6-$CF_3$ | 2-furyl | $4CH_3C_6H_4$ |
| 4-$NO_2$ | 7-Cl | 2-furyl | $C_6H_5$ |
| 5-Br | 6-$CH_3$ | 2-furyl | $4\text{-}ClC_6H_4$ |

PREPARATION A

1-(3-Thienyl)indole

A mixture of indole (16 g, 0.136 M), 3-bromothiophene (24.75 g, 0.146 M), potassium carbonate (20.1 g, 0.146 M) and copper bromide (0.84 g, 0.003 M) in 160 ml of N-methyl-2-pyrrolidinone was stirred and heated to 180° C. (under nitrogen atmosphere) for 42 hours. After this time, the reaction mixture was poured onto 800 ml of water and extracted with ethyl acetate (2×350 ml). The combined ethyl acetate extracts were washed with water, brine, dried over magnesium sulfate, filtered and concentrated in vacuo leaving a dark brown-black oil. The crude reaction product was chromatographed on a silica gel column with hexane/$CH_2Cl_2$ 3:1 as eluant. Yield=9.14 g of yellow liquid which was homogeneous by thin layer chromatography. MS: $M^+ = 199$.

Analysis calculated for $C_{12}H_9NS$: C, 72.32; H, 4.55; N, 7.23%.

Found: C, 72.06; H, 4.71; N, 7.47%.

In like manner the following 1-(heteroaryl)indoles are prepared from the appropriate bromoheteroaryl reactant:

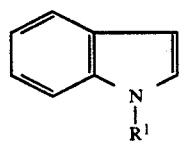

| R¹ | MS: $M^+$ |
|---|---|
| 2-thienyl | 199 |
| 3-furyl[a] | 183 |
| | (100) |
| 2-thiazolyl[b] | 200 |
| | (100) |

[a] $R_f(CH_2Cl_2) = 0.67$
[b] a 100% excess of 2-thiazolyl bromide was used. $R_f$ of product in $CH_2Cl_2 = 0.45$.

PREPARATION B

1-(3-Thienyl)oxindole

To a solution of 1-(3-thienyl)indole (9.14 g, 0.0459 M) in 350 ml of dry methylene chloride under a nitrogen atmosphere was added 6.44 g (0.0482 M) of N-chlorosuccinimide (NCS) at room temperature. The reaction was stirred at room temperature for 2 hours, then concentrated in vacuo. The resulting foamy residue was immediately dissolved in 190 ml of glacial acetic acid. The resulting mixture was heated to 70° C. followed by the addition of 49.5 ml of 85% $H_3PO_4$ and heating of the reaction mixture to reflux for one hour. The mixture was then cooled to room temperature, poured onto ice water, basified to pH ~11–12 with $Na_2CO_3$ and extracted with ethyl acetate (3×500 ml). The combined ethyl acetate extracts were washed with water, brine, dried (MgSO₄), filtered and concentrated in vacuo leaving dark brown-black oil. Purification of the crude product on a silica gel column (elution with $CH_2Cl_2$, followed by elution with 90% $CH_2Cl_2$—10% $CH_3OH$) gave a total of 7.2 grams (72.8%) of brown crystalline solid; m.p. 62°–67° C. MS: $M^+ = 215$. IR(KBr) 5.9 μ(s) c=O. NMR(CDCl₃)delta: 3.6 (s, 2H), 6.7–7.4 (m, 7H).

The following 1-(heteroaryl)indoles are prepared according to the above procedure from the products of Preparation A.

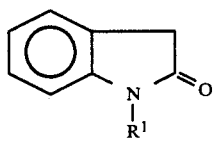

| R¹ | MS: M+ |
|---|---|
| 2-thienyl | 215 |
| 3-furyl[a] | 199 (100) |
| 2-thiazolyl[b] | 216 (78) |

[a] 1H-NMR(CDCl₃)delta: 7.8–6.6(m, 7H), 3.55(s, 2H).
[b] TLC (3% CH₃OH/CH₂Cl₂): $R_f$ = 0.35
[1] H-NMR(CDCl₃)delta: 7.0–7.6(m, 6H), 3.6(s, 2H).

PREPARATION C

Starting with the appropriate substituted indole and R¹Br reactants, the following compounds are prepared according to the procedure of Preparation A.

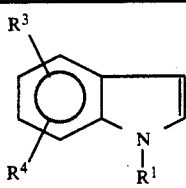

| R³ | R⁴ | R¹ |
|---|---|---|
| 4-F | H | 3-thienyl |
| 5-F | H | 3-thienyl |
| 6-F | H | 3-thienyl |
| H | 7-F | 3-thienyl |
| 4-Cl | H | 3-thienyl |
| 5-Cl | H | 3-thienyl |
| 6-Cl | H | 3-thienyl |
| H | 7-Cl | 3-thienyl |
| 6-CF₃ | H | 3-thienyl |
| 5-CH₃ | H | 3-thienyl |
| H | 7-C₂H₅ | 3-thienyl |
| 6-Br | H | 3-thienyl |
| 4-OCH₃ | H | 3-thienyl |
| 4-SCH₃ | H | 3-thienyl |
| 5-NO₂ | H | 3-thienyl |
| 4-OCH₃ | 6-OCH₃ | 3-thienyl |
| 4-Cl | 5-NO₂ | 3-thienyl |
| 5-CH₃ | 7-Cl | 3-thienyl |
| 5-Cl | 6-Cl | 3-thienyl |
| 5-F | 6-F | 3-thienyl |
| 4-CH₃ | 7-CH₃ | 3-thienyl |
| 5-OCH₃ | 6-Cl | 3-thienyl |
| 5-OCH₃ | 6-F | 3-thienyl |
| H | 7-i-C₄H₉ | 3-thienyl |
| 5-F | H | 2-thienyl |
| 6-F | H | 2-thienyl |
| 5-Cl | H | 2-thienyl |
| 5-CF₃ | H | 2-thienyl |
| 5-CH₃ | H | 2-thienyl |
| 6-Br | H | 2-thienyl |
| 4-SCH₃ | H | 2-thienyl |
| 4-OCH₃ | 6-OCH₃ | 2-thienyl |
| 5-CH₃ | 7-Cl | 2-thienyl |
| 5-F | 6-F | 2-thienyl |
| 5-OCH₃ | 6-F | 2-thienyl |
| 5-CF₃ | H | 2-thienyl |
| 5-F | H | 3-furyl |
| 6-Cl | H | 3-furyl |
| 4-SCH₃ | H | 3-furyl |
| 6-CF₃ | H | 3-furyl |
| 6-Br | H | 3-furyl |
| 4-SCH₃ | H | 3-furyl |
| 6-NO₂ | H | 3-furyl |
| 4-Cl | 6-Cl | 3-furyl |
| 7-CH₃ | H | 3-furyl |
| H | 7-i-C₄H₉ | 3-furyl |
| 5-Br | 7-CH₃ | 3-furyl |
| 5-CH₃ | 6-CH₃ | 3-furyl |
| 5-OCH₃ | 6-OCH₃ | 3-furyl |
| 5-OCH₃ | 6-Cl | 3-furyl |
| 5-F | H | 2-furyl |
| 5-Cl | H | 2-furyl |
| 6-CF₃ | H | 2-furyl |
| 4-SCH₃ | H | 2-furyl |
| 5-NO₂ | H | 2-furyl |
| 5-OCH₃ | 6-Cl | 2-furyl |
| 5-OCH₃ | 6-OC₂H₅ | 2-furyl |
| 5-CH₃ | 7-Cl | 2-furyl |
| 5-Cl | 7-Cl | 2-furyl |
| 6-i-C₃H₇ | H | 2-furyl |
| 4-NO₂ | 7-Cl | 2-furyl |
| 5-OCH₃ | 6-F | 2-furyl |
| 5-Br | 7-CH₃ | 2-furyl |
| 5-F | H | 2-thiazolyl |
| 6-F | H | 2-thiazolyl |
| 5-Cl | H | 2-thiazolyl |
| 5-Br | H | 2-thiazolyl |
| H | 7-C₂H₅ | 2-thiazolyl |
| 6-CF₃ | H | 2-thiazolyl |
| 5-CH₃ | H | 2-thiazolyl |
| 6-NO₂ | H | 2-thiazolyl |
| 6-i-C₃H₇ | H | 2-thiazolyl |
| 4-OCH₃ | 7-OCH₃ | 2-thiazolyl |
| 5-OCH₃ | 6-OCH₃ | 2-thiazolyl |
| 5-CH₃ | 6-CH₃ | 2-thiazolyl |
| 5-OCH₃ | 6-F | 2-thiazolyl |
| 4-SCH₃ | H | 2-thiazolyl |
| 5-CH₃ | 6-Cl | 2-thiazolyl |
| 4-NO₂ | 7-Cl | 2-thiazolyl |
| 5-Cl | 7-Cl | 2-thiazolyl |

PREPARATION D

The compounds of Preparation C are converted to the corresponding oxindoles having the formula shown below by means of the procedure of Preparation B:

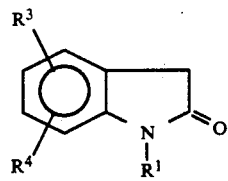

I claim:
1. A compound of the formula (I)

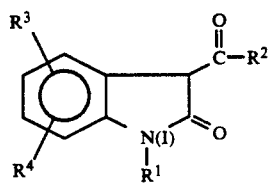

or a pharmaceutically acceptable base salt thereof wherein

R$^1$ is thienyl, furyl or 2-thiazolyl;

R$^2$ is thienyl, furyl or

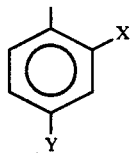

wherein X is hydrogen, fluoro, chloro, alkyl having 1 to 4 carbon atoms, alkoxy having 1 to 4 carbon atoms, alkylthio having 1 to 4 carbon atoms, nitro or trifluoromethyl;

Y is hydrogen, fluoro or chloro;

and each of R$^3$ and R$^4$, which may be alike or different, is hydrogen, fluoro, chloro, bromo, alkyl having 1 to 4 carbon atoms, alkoxy having 1 to 4 carbon atoms, alkylthio having 1 to 4 carbon atoms, nitro or trifluoromethyl.

2. A compound according to claim 1 wherein R$^1$ is thienyl.

3. A compound according to claim 2 wherein R$^1$ is 3-thienyl and R$^2$ is

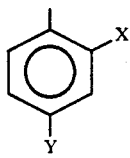

4. A compound according to claim 3 wherein X is H, F, Cl, S(C$_{1-4}$)alkyl or CF$_3$; and Y is H, F or Cl; and each of R$^3$ and R$^4$ is hydrogen.

5. The compound according to claim 4 wherein each of X and Y is F.

6. The compound according to claim 4 wherein each of X and Y is Cl.

7. A compound according to claim 2 wherein R$^1$ is 2-thienyl and R$^2$ is

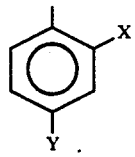

wherein each of X and Y is H, F or Cl; and each of R$^3$ and R$^4$ is hydrogen.

8. The compound according to claim 7 wherein each of X and Y is H.

9. The compound according to claim 7 wherein each of X and Y is F.

10. A compound according to claim 1 wherein R$^1$ is furyl.

11. A compound according to claim 10 wherein R$^1$ is 3-furyl and R$^2$ is

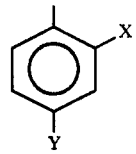

12. A compound according to claim 11 wherein each of X and Y is H, F or Cl; and each of R$^3$ and R$^4$ is hydrogen.

13. The compound according to claim 12 wherein each of X and Y is H.

14. The compound according to claim 12 wherein each of X and Y is F.

15. A method of treating an inflammatory disease in a mammal which comprises administering to said subject an inflammatory disease treating amount of a compound of the formula

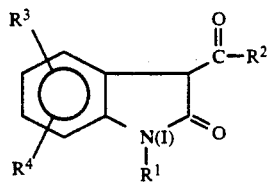

or a pharmaceutically acceptable base salt thereof wherein

R$^1$ is thienyl, furyl or 2-thiazolyl;

R$^2$ is thienyl, furyl or

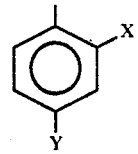

wherein X is hydrogen, fluoro, chloro, alkyl having 1 to 4 carbon atoms, alkoxy having 1 to 4 carbon atoms, alkylthio having 1 to 4 carbon atoms, nitro or trifluoromethyl;

Y is hydrogen, fluoro or chloro;

and each of R$^3$ and R$^4$, which may be alike or different, is hydrogen, fluoro, chloro, bromo, alkyl having 1 to 4 carbon atoms, alkoxy having 1 to 4 carbon atoms, alkylthio having 1 to 4 carbon atoms, nitro or trifluoromethyl.

16. A pharmaceutical composition, useful as an antiinflammatory agent in a mammal, comprising a pharmaceutically-acceptable carrier and an inflammatory disease treating amount of a compound according to claim 1.

* * * * *